United States Patent [19]

Hausinger

[11] Patent Number: 5,846,752
[45] Date of Patent: Dec. 8, 1998

[54] MUTANT UREASE AND METHOD OF USE FOR DETERMINATION OF UREA

[75] Inventor: Robert P. Hausinger, East Lansing, Mich.

[73] Assignee: Board of Trustees operating Michigan State University, East Lansing, Mich.

[21] Appl. No.: 687,645

[22] Filed: Jul. 26, 1996

[51] Int. Cl.⁶ .............................. C12Q 1/58; C12P 13/02; C12N 9/78

[52] U.S. Cl. ............................ 435/12; 435/128; 435/227; 435/41

[58] Field of Search .............................. 435/12, 227, 128, 435/41

[56] References Cited

U.S. PATENT DOCUMENTS

| | | | |
|---|---|---|---|
| 3,145,086 | 8/1964 | Free et al. .................................. | 23/253 |
| 4,066,403 | 1/1978 | Bruschi ..................................... | 23/230 |
| 4,218,535 | 8/1980 | Ray ........................................... | 435/12 |
| 5,037,738 | 8/1991 | Lamos et al. ............................. | 435/12 |
| 5,093,255 | 3/1992 | Kakimoto et al. ....................... | 435/183 |
| 5,137,692 | 8/1992 | Fritz ......................................... | 422/61 |
| 5,298,399 | 3/1994 | Uozumi et al. .......................... | 435/69.1 |

OTHER PUBLICATIONS

Park, I.-S. "Mechanistic studies of Klebsiella aerogenes urease and its nickel metallocenter assembly process" Dissertation Abstracts International (1994), vol. 56, No. 3B, p. 1396.

Mulrooney, S.B. and Hausinger, R.P., Journal of Bacteriology 172:5837–5843 (1990).

Park, I.–S. and Hausinger, R.P., Protein Science 2:1034–1041 (1993).

Mulrooney, et al., J. Gen. Microbiol. 135: 1769–1776 (1989).

Kunkel et al, Proc. Natl. Acad. Sci. 82: 488: 492 (1985).

Sanger, et al., Proc. Natl. Acad. Sci. USA 74:5463–5467 (1977).

Sambrook et al., Molecular Cloning: A Laboratory Manual. Cold Spring Harbor Laboratory, Cold Spring Harbor, New York (1989) pp. 13.42–13.43.

Todd & Hausinger, J. Biol. Chem. 264:15835–15942 (1989).

Weatherburn, M.W., Anal. Chem. 39:971–974 (1967).

Wilkinson, G.N., Biochem. J. 80:324–332 (1961).

Lowry et al., J. Biol. Chem. 193:265–275 (1951).

*Primary Examiner*—Robert A. Wax
*Assistant Examiner*—Kawai Lau
*Attorney, Agent, or Firm*—Ian C. McLeod

[57] ABSTRACT

A mutant urease of *Klebsiella aerogenes* characterized as αH219Q having a glutamine (Q) in position 219 in place of histidine (H). The resulting enzyme has a low affinity for substrate (high value of $K_m$) and is particularly useful in assays and test kits for measuring urea concentrations in body fluids.

4 Claims, 7 Drawing Sheets

```
241  CCCGAATCTGGCTGACTTAAGAGAACGTTATGGAACTGACCCCCGAGAAAAGACAAG        300
                              MetGluLeuThrProArgGluLysAspLys

301  CTGTTGCTGTTTACCGCCGCTGGTGGCGCTGGGCGGTTGCGGCCTGAAGCTC              360
     LeuLeuLeuPheThrAlaAlaLeuValAlaGluAlaArgArgLeuAlaArgGlyLeuLysLeu

361  AACTATCCGGAGTCCGTGGCCCTGATCAGCGCCCTTTATTATGGAAGGCGCTCGGACGGC     420
     AsnTyrProGluSerValAlaLeuIleSerAlaPheIleMetGluGlyAlaArgAspGly

421  AAAAGCGTGGCCTCGCTGATGGAGGAAGCCGTCACGTCCTGACCCGCGAGCAGGTGATG      480
     LysSerValAlaSerLeuMetGluGlyHisValLeuThrArgGluGlnValMet

481  GAGGGCGTCCCGGAAATGATCCCGGATATCCAGGTCGAAGCCACCTTCCCGGACGGCTCG    540
     GluGlyValProGluMetIleProAspIleGlnValGluAlaThrPheProAspGlySer

541  AAGCTGGTCACCGTTCACAACCCGATTATCTGAGGTAGCGCCATGATCCCCGGTGAATAT   600
     LysLeuValThrValHisAsnProIleIleEnd        MetIleProGlyGluTyr

601  CACGTTAAGCCCGGTCAGATAGCCCTGAATACCGGGCAACCTGTCGCGTGGTCGTT        660
     HisValLysProGlyGlnIleAlaLeuAsnThrGlyArgAlaThrCysArgValValVal

661  GAGAACCACGGCGATCGGCGTTCAGGTCGCCACTACCATTCGCCGAGGTTAAC           720
     GluAsnHisGlyAspArgProIleGlnValGlyLysSerHisTyrHisPheAlaGluValAsn

721  CCGGGCGCTGAAGTTCGACCGTCAGCAGGCCGGCTATCGCCTGAATATCCCGGGGGC       780
     ProAlaLeuLysPheAspArgGlnGlnAlaGlyTyrArgLeuAsnIleProAlaGly

781  ACGGGCGGTACGCTTTGAACCCGGCCAGAAACGCGAGGTCGAGCTGGTGGCCTTCGCCGGT   840
     ThrAlaValArgPheGluProGlyGlnLysArgGluValGluLeuValAlaPheAlaGly
```

FIG. 1A

```
 841  CACCGCGCCGTCTTCGGCTTCCGCGGCGAGGTCATGGGCCCTCTGGAGGTAAACGATGAG    900
      HisArgAlaValPheGlyPheArgGlyGluValMetGlyProLeuGluValAsnAspGlu
                                                             MetSe
 901  TAATATTTCACGCCCAGGCCTATGCCGATATGTTCGGCCCCACCGTCGGCGACAAGGTGCG    960
      End
      rAsnIleSerArgGlnAlaTyrAlaAspMetPheGlyProThrValGlyAspLysValAr
 961  CCTGGCAGATACCGAGCTGTGGATCGAGGTGGAGGACGATTTGACCACCTACGGGAAGA   1020
      gLeuAlaAspThrGluLeuTrpIleGluValGluAspAspLeuThrThrTyrGlyGluGl
1021  GGTCAAATTCGGCGGGCAAAGTGATCCGCGACGGCATGGGCCAGGACAGATGCTGGC    1080
      uValLysPheGlyGlyGlyLysValIleArgAspGlyMetGlyGlnMetLeuAl
1081  CGCCGACTGTGTCGACCTGGTCGCTCACCAACGCGTTGATCGTCGATCACTGGGGATCGT   1140
      aAlaAspCysValAspLeuValAspLeuValLeuThrAsnAlaLeuIleValAspHisTrpGlyIleVa
1141  TAAGGCCGATATCGGCGTGAAGGACGGCCGATCTTCGCCATCGGCAAAGCCGGCAACCC   1200
      lLysAlaAspIleGlyValLysAspGlyArgIlePheAlaIleGlyLysAlaGlyAsnPr
1201  CGACATCCAGCCCAACGTCACCATCCCCATCCCGGCTGCGACGGAAGTGATCGCCGCCGA   1260
      oAspIleGlnProAsnValThrIleProIleGlyAlaAlaThrGluValIleAlaAlaGl
1261  AGGAAAAATTGTCACCGCCGGCGGATCGATACCCATATTCACTGGATCTGTCCGCAGCA   1320
      uGlyLysIleValThrAlaGlyGlyIleIleAspThrHisIleHisTrpIleCysProGlnGl
      ʌ [[K
1321  GGCGGAAGAGGCGCTGGTCTCTGGCGTGACCACCATGGTCGGGCACCGGGCCCGGC    1380
```

```
1801  GCCCTACACCCTCAACACCATCGATGAACATCTCGATATGCTGATGGTCTGCCACCATCT  1860
      uProTyrThrLeuAsnThrIleAspGluHisLeuAspMetLeuMetValCysHisHisLe

1861  GGACCCGGACACATCGCCGAGGACGTGCTGGCCTTTGCCGAGTCGCCGCATTCGCCGAAACCAT  1920
      uAspProAspIleAlaGluAspValAlaPheAlaGluSerArgIleArgArgGluThrIl

1921  CGCTGCGGAAGACGTGCTGCACGATCTCGGCGCCTTCTCGCTCACCTCCTCCGATTCGCA  1980
      eAlaAlaGluAspValLeuHisAspLeuGlyAlaPheSerLeuThrSerSerAspSerGl

1981  GGCCATGGGCCGCGTCGGGGAAGTGATTCTCCGCACCTGGCAGGTGGCCATCGCATGAA  2040
      nAlaMetGlyArgValGlyGluValIleLeuArgThrTrpGlnValAlaHisArgMetLy

2041  GGTGCAGCGCGGCGAGCGCTGGCGGAGGAGAGGGATAACGGGGGATAACAACTTCCGCGTGAAGCG  2100
      sValGlnArgGlyAlaLeuAlaGluAlaLeuThrGlyAspAsnAsnPheArgValLysAr

2101  CTACATCGCCAAATACACCATCAACCCGGCGCTGACCCACGGCATCGCACACGAAGTCGG  2160
      gTyrIleAlaLysTyrThrIleAsnProAlaLeuThrHisGlyIleAlaHisGluValGl

2161  ATCCATTGAGGTGGGTAAGCTGGTCGACCTCGTGGTCACCAGCCTTCTTCGGCGT  2220
      ySerIleGluValGlyLysLeuAlaAspLeuValValTrpSerProAlaPhePheGlyVa
```

FIG. ID

```
2221  GAAACCGGCCACCGTGATCAAAGGCGGCATGATCGCCATCGCGCCGATGGGCGATATCAA   2280
      lLysProAlaThrValIleLysGlyGlyMetIleAlaIleAlaProMetGlyAspIleAs

2281  TGCCTCTATTCCGACCCCGCAGCCGGTGCACTACCGCCCGATGTTTGGCGCTGGCGGCAG   2340
      nAlaSerIleProThrProGlnProValHisTyrArgProMetPheGlyAlaLeuGlySe

2341  CGCCCGCCATCACTGCCGCCTCACCTTCCTGTCGCAGGGCGGCAGCCAATGGCGTTGC    2400
      rAlaArgHisHisCysArgLeuThrPheLeuSerGlnAlaAlaAlaAlaAsnGlyValAl

2401  CGAGCGGCTGAACCTGCGCGCAGCGGCGATCGCGCTGGTGAAAGGCTGCCGTACGGTGCAGAA   2460
      aGluArgLeuAsnLeuArgSerAlaIleAlaValValLysGlyCysArgThrValGlnLy

2461  AGCCGACATGGTGCACAACAGTCTGCAGCCCTAACATCACCGTCGACGCCCAGACCTATGA   2520
      sAlaAspMetValHisAsnSerLeuGlnProAsnIleThrValAspAlaGlnThrTyrGl

2521  GGTGCGGGTGGATGGCGAACTTATCACCAGCGAGCCGGCAGACGTTCTGCCGATGGCCA   2580
      uValArgValAspGlyGluLeuIleThrSerGluProAlaAspValLeuProMetAlaGl

2581  ACGATATTTCTGTTTAAGGAGAGCGGATGCTTTATTTAACTCAACGTCTGGAGATCCC    2640
      nArgTyrPheLeuPheEnd
```

FIG. 1E

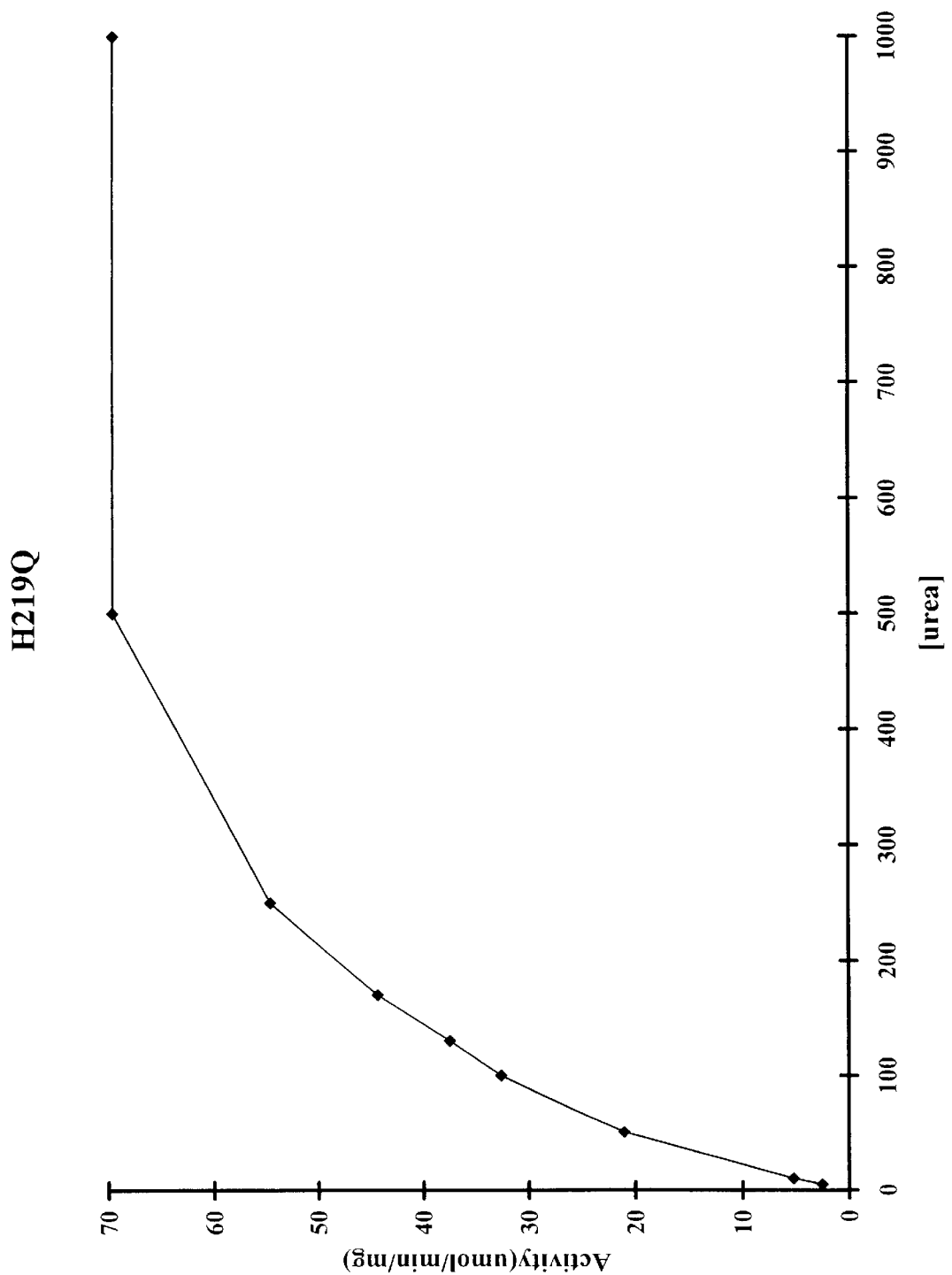

MUTANT UREASE AND METHOD OF USE FOR DETERMINATION OF UREA

GOVERNMENT RIGHTS

This invention was made with government support under Grant No. 91-37305-6515 by the United States Department of Agriculture. The government has certain rights in the invention.

BACKGROUND OF THE INVENTION

(1) Summary of the Invention

The present invention relates to the use of a mutant urease to convert urea to carbonic acid and ammonia, particularly in an assay to measure urea concentrations. In particular, the present invention relates to the mutant urease which is characterized as αH219Q.

(2) Description of Related Art

*Klebsiella aerogenes* urease and the DNA encoding it are described by Mulrooney, S. B. and Hausinger, R. P., in Journal of Bacteriology 172:5837–5843 (1990). The urease genes include ureA, ureB and ureC encoding the γ, β and α subunits of the enzyme.

Mutagenesis of various sites in the urease DNA of *Klebsiella aerogenes* is described by Park, I.-S. and Hausinger, R. P., in Protein Science 2:1034–1041 (1993). In particular, position 219 of the α subunit (αH219) was modified from histidine (H) to alanine (A). This change resulted in a diminishment of specific activity and an increase in the value of $K_m$ for the purified enzyme. Thus it was determined that the amino acid at position 219 was important to the binding affinity of urease to the substrate (urea).

The prior art has described numerous methods and test kits for using urease to assay for urea in body fluids, such as urine and blood plasma, and other biological materials. The presence of abnormal levels of urea is indicative of disease. Various calorimetric methods are used to detect a pH change or to otherwise detect the reaction products. Illustrative of the extensive prior art are U.S. Pat. Nos. 3,145,086 to Free et al; 4,066,403 to Bruschi; 4,218,535 to Ray; 5,093,255 to Kakimoto et al; 5,037,738 to Lamos et al; 5,137,692 to Fritz, and 5,298,399 to Uozumi et al. Ureases are thus commercially important, particularly in the medical field, although they do have non-medical uses.

OBJECTS

An object of the present invention is to provide a mutant urease which has improved enzyme kinetic properties (higher $K_m$) compared to the natural enzyme. Further, it is an object of the present invention to provide a method and test kit for use of the mutant urease, particularly in an assay of urea concentrations in body tissues. These and other objects will become increasingly apparent by reference to the following description and the drawing.

IN THE DRAWINGS

Figure 1C:
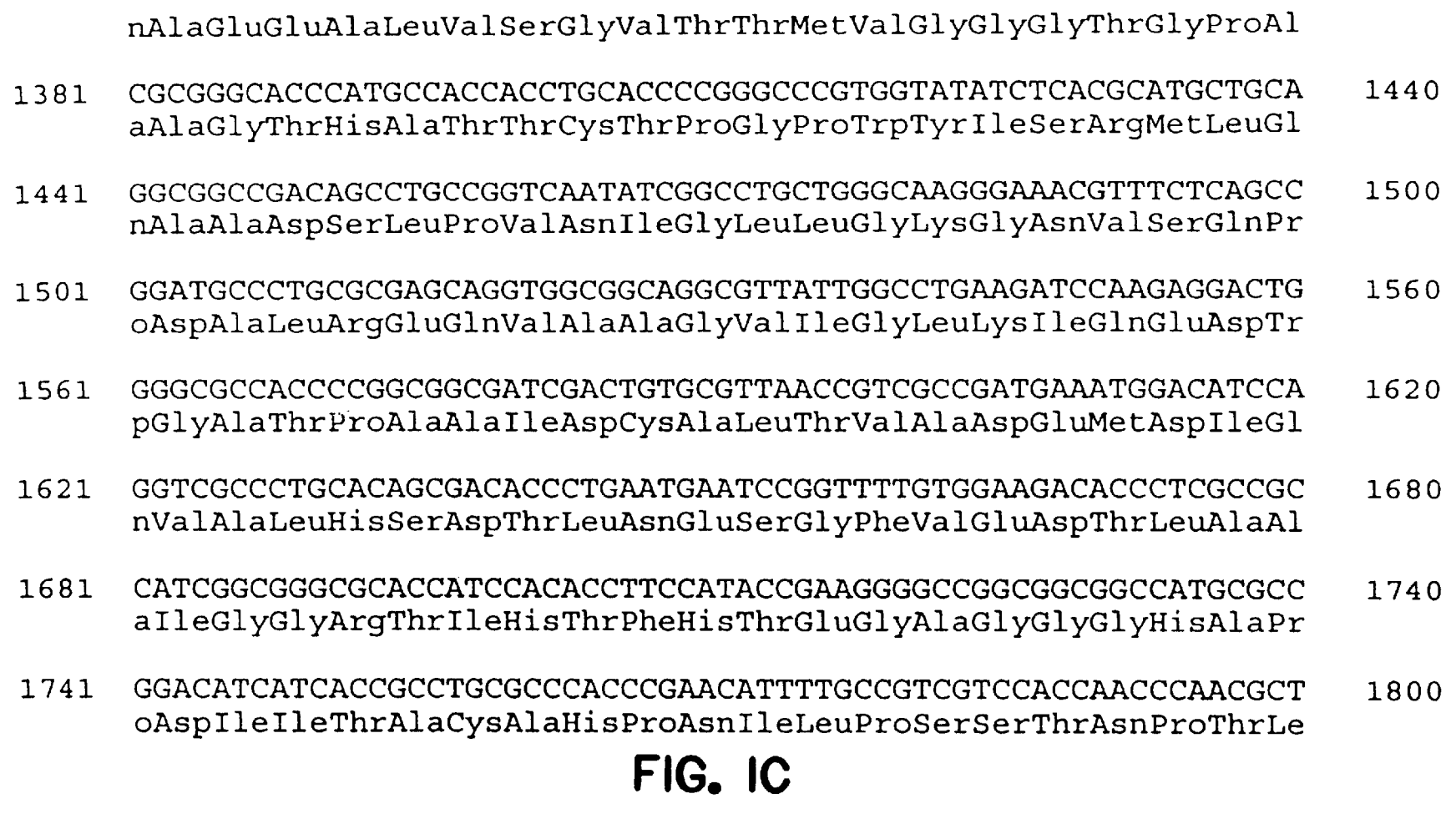

FIG. 1A to 1E show the nucleotide sequence encoding urease.

FIG. 3 is a graph showing activity of urease αH21Q versus concentration of urea in mM.

DESCRIPTION OF PREFERRED EMBODIMENTS

Figure 2:
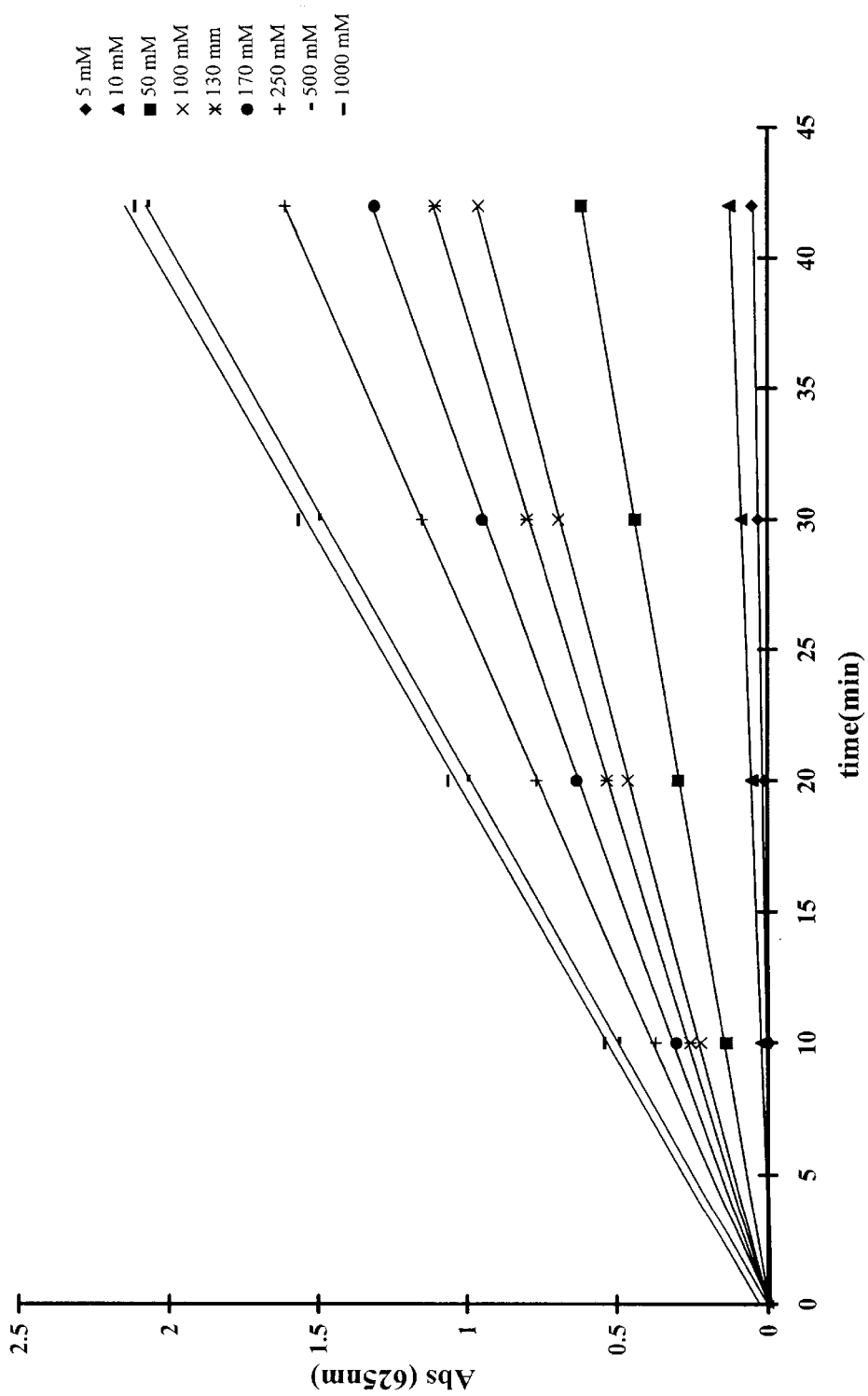
FIG. 2 is a graph showing absorbance arising from conversion of released ammonia into indophenol as a function of time for urease αH219Q incubated at different concentrations of urea.

The present invention relates to a urease of *Klebsiella aerogenes* having a modified urease α subunit, designated as αH219Q, having glutamine as substituent number 219 of the α subunit as set forth in SEQ ID NO: 5.

The present invention also relates to a method for converting urea to carbonic acid and ammonia with an enzyme, the improvement which comprises using a urease of *Klebsiella aerogenes* having a modified a subunit, designated as H219Q, having glutamine as substituent 219 of the α subunit for the conversion as set forth in SEQ ID NO: 5, wherein the urease has a low affinity for the urea and thus a higher $K_m$ as compared to αH219.

The present invention further relates to a method for assaying for urea in a body fluid by conversion of the urea to carbonic acid and ammonia as products with a urease and detecting the products, the improvement which comprises using a urease of *Klebsiella aerogenes* having a modified α subunit, designated as H219Q, having glutamine as substituent 219 of the α subunit as set forth in SEQ ID NO: 5 for the conversion to the products in the assay which are then detected.

The present invention further relates to a test kit for assaying for urea in a body fluid by conversion of urea to carbonic acid and ammonia as products with an enzyme including a means for detecting one or more of the products of the urea, the improvement which comprises: providing in the kit a urease of *Klebsiella aerogenes* having glutamine as substituent 219 of the α subunit as set forth in SEQ ID NO: 5 for use to make the conversion.

The segment of urease is referred to as UreA, UreB and UreC. The gene is referred to in the same manner except the first letter is lower case and the gene designation is in italics (ureA, ureB and ureC).

The nucleotide sequence encoding H219Q mutant urease is set forth in SEQ ID NO: 1. The UreA peptide is encoded by nucleotides 271–573 in this sequence (SEQ ID NO: 3). UreB is encoded by nucleotides 583–903 (SEQ ID NO: 4). UreC is encoded by nucleotides 896–2599 (SEQ ID NO: 5). This sequence is identical to that in the wild-type organism except for one base pair change at position 1552 (within ureC) that was mutated by using the following oligonucleotide primer: GAAGATCCAAGAGGACTGG (SEQ ID NO: 2). The DNA is contained in plasmid pKAU17αH219Q in the bacterium in *Escherichia coli* strain DH5. This strain was deposited on Jul. 12, 1996 under the Budapest Treaty with the American Type Culture Collection, Rockville, Md. as ATCC 98103. The strain is available subject to the provisions of the Budapest Treaty and the patent laws.

EXAMPLE 1

Site directed mutagenesis was used to create a mutant capable of forming αH219Q urease, and the protein was partially purified and characterized.

Site-directed mutagenesis

For generation of αH219Q, a 1.4-kb SacI-SmaI fragment of pKAU17 (Mulrooney et al., J. Gen. Microbiol. 135:1769–1776 (1989)) was subcloned into M13 mp18 and mutagenized by the method of Kunkel et al (Proc. Natl. Acad. Sci. 82:488–492 (1985)). A 1.1-kb BamH1-SalI fragment of plasmid was used. Uracil-containing single-stranded template DNA was prepared from *E. coli* CJ236 (dut1 ung1 thi-1 relAl/pCJ105[cam'F']). Mutagenized phage were isolated in *E. coli* MV1193 (Δ[lacI-proAB] rpsL thi endA spcB15 hsdR4 Δ[sr1-recA]306::Tn10[tet$^r$] F'[traD36 proAB+lacI$^q$ lacZΔM15). The oligonucleotide was synthesized by using an Applied Biosystems Model 394 DNA synthesizer at the Michigan State University Macromolecular Structural Facility, East Lansing, Mich. GAAGATC- CAAGAGGACTGG (SEQ ID NO: 2). This primer was used to alter the conserved histidine codon αH219 to encode glutamine. Site-directed mutants were identified by DNA sequencing and subcloned back into pKAU17 on a 0.8-kb MluI-BamI fragment. These regions were completely sequenced by using Sequenase 2.0 (United States Biochemicals) and the single-strand DNA sequencing method of Sanger et al, Proc. Natl. Acad. Sci. USA 74:5463–5467 (1977) to ensure that no other mutations had been introduced into M13. After subcloning, the mutated sequences were again confirmed by double-strand DNA sequencing methods (Sambrook et al., Molecular Cloning: A Laboratory Manual. Cold Spring Harbor Laboratory, Cold Spring Harbor, N.Y. (1989)).

Enzyme Purification

The urease was partially purified from *E. coli* DH5 carrying the site-directed mutant of pKAU17 by procedures described previously (Todd & Hausinger, J. Biol. Chem. 264:15835–15942 (1989)), except that cells were grown in LB medium containing 1 mM $NiCl_2$.

Assay of enzyme activity

Urease activity for αH219Q enzyme was assayed in 25 mM MES, pH 6.2, or 25 mM HEPES, pH 7.75, 0.5 mM EDTA, and 1M urea (the urea concentration was varied for kinetics measurements). One unit of enzyme activity is defined as the amount of enzyme required to degrade 1 μmol of urea per minute at 37° C. FIG. 2 shows the results at various concentrations of urea. Linear regression analysis of the released ammonia, determined by conversion to indophenol (Weatherburn, M. W., Anal. Chem. 39:971–974 (1967)), versus time yielded the initial rates. A plot of initial rates as a function of urea concentration is shown in FIG. 3. For comparison, analogous studies with the wild type enzyme (Todd and Hausinger, J. Biol. Chem. 264:15835–15942 (1989)) show that maximal rates are achieved by approximately 15 mM urea concentration. Calculation of kinetic constants made use of the method of Wilkinson, G. N., Biochem. J. 80:324–332 (1961). Protein was assayed by the method of Lowry et al, J. Biol. Chem. 193:265–275 (1951)).

Urease H219Q has a $K_m$ value of approximately 175 mM or about 75-fold that of the native enzyme. The rate of H219Q enzyme at its pH optimum (pH 6.2) is about 45% of that measured for the wild-type urease at its pH optimum at pH 7.75.

EXAMPLE 2

Feasibility studies to demonstrate the usefulness of H219Q urease in a test kit for analysis of urea levels in body fluids.

Approximately 0.75 mg aliquots of H219Q urease were diluted with 5 ml of either 10 mM citric acid, 10 mM MES, 10 mM HEPES, or 10 mM phosphate buffers (pH 6.2 in all cases), each containing the pH indicator phenol red at a concentration of 0.04%. The solutions were used to wet cellulose strips which were then allowed to air dry, resulting in yellow-colored test strips. Samples (5 μl) containing urea at concentrations of 0.01, 0.02, 0.05, 0.10, 0.20, 0.33, 0.50, and 1.0M were added to each of the test strips. The times (in seconds) required to detect pink coloration at the sites of addition were measured. Sample data is tabulated below:

TABLE 1

H219Q Urease Test Kit Feasibility Study

| Concentration of Urea (M) | Time required (sec) for formation of pink color in the following buffers | | | |
|---|---|---|---|---|
| | Citrate | MES | HEPES | Phosphate |
| 0.01 | 110 | 200 | 120 | 240 |
| 0.02 | 42 | 87 | 56 | 68 |
| 0.05 | 26 | 40 | 27 | 40 |
| 0.10 | 20 | 28 | 18 | 27 |
| 0.20 | 9 | 12 | 9 | 14 |
| 0.33 | 6 | 9 | 6 | 10 |
| 0.50 | 4 | 6 | 4 | 6 |
| 1.0 | 3 | 5 | 3 | 5 |

Various pH indicators, such as bromothymol blue or bromocresol purple can be used. There is little dependence on the buffer used in the assay, but citrate or HEPES buffers appear to allow the most rapid development of color, whereas, color development is slower in MES or phosphate buffers. The time required for color development can be adjusted by altering the amount of enzyme impregnated into the test strip. In addition, the endpoint can be varied by monitoring the time required for the test strip color intensities to reach that of a colored gage that could be included in a kit. These results demonstrate that test strips containing H219Q enzyme can be used for simple, rapid, and reliable measurements of urea concentrations over a concentration range that is clinically useful.

This procedure is readily adaptable to use in a test kit with a variety of formats including a test strip or sheet made of a wide variety of materials well known to those skilled in the art. The kit could also include ingredients in separate containers which are combined for a testing as is also well known. Preferably the ingredients are in a dry form and water is added in a solution with the urea. Body fluid samples can be added directly to the dry urease, any buffers and the indicator. Various indicators are well known to those skilled in the art which react with the products produced (ammonium carbonate) or the urea, or a change in condition of the reaction solution (such as pH).

I claim:

1. A urease of *Klebsiella aerogenes* having a modified urease α subunit, designated as αH219Q, having glutamine as substituent number 219 of the α subunit as set forth in SEQ ID NO: 5 and having an optimum pH of 6.2 with a rate with urea as a substrate that is about 45% of that of the urease of the *Klebsiella aerogenes*.

2. In a method for converting urea to carbonic acid and ammonia with an enzyme, the improvement which comprises using the αH219Q variant of urease of *Klebsiella aerogenes* having a modified α subunit, designated as H219Q, having glutamine as substituent 219 of the α subunit for the conversion as set forth in SEQ ID NO: 5, wherein the urease has a low affinity for urea and thus a higher $K_m$ as compared to αH219 and having an optimum pH of 6.2 with a rate with urea as a substrate that is about 45% of that of the urease of the *Klebsiella aerogenes*.

3. In a method for assaying for urea in a body fluid by conversion of the urea to carbonic acid and ammonia as products with a urease and detecting the products, the improvement which comprises using a urease of *Klebsiella aerogenes* having a modified α subunit, designated as H219Q, having glutamine as substituent 219 of the α subunit as set forth in SEQ ID NO: 5 for the conversion to the products in the assay which are then detected, wherein the urease has a low affinity for the urea and thus a higher $K_m$ as compared to αH219 and having an optimum pH of 6.2 with a rate with urea as a substrate that is about 45% of that of the urease of the *Klebsiella aerogenes*.

4. In a test kit for assaying for urea in a body fluid by conversion of urea to carbonic acid and ammonia as products with an enzyme including a means for detecting one or more of the products of the urea, the improvement which comprises:

providing in the kit a urease of *Klebsiella aerogenes* having glutamine as substituent 219 of the α subunit as set forth in SEQ ID NO: 5 and having an optimum pH of 6.2 with a rate with urea as a substrate that is about 45% of that of the urease of the *Klebsiella aerogenes* for use to make the conversion.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 2400
( B ) TYPE: nucleotides (C) STRANDEDNESS: Single
(D) TOPOLOGY: Linear (ii) MOLECULE TYPE:
    (A) DESCRIPTION: cDNA (iii) HYPOTHETICAL: No (iv) ANTI-SENSE: No (vi) ORIGINAL SOURCE:
    (A) ORGANISM: Klebsiella aerogenes
    (B) STRAIN: CG253
    (C) INDIVIDUAL ISOLATE:
    (G) CELL TYPE: N/A (ix) FEATURE:
    (A) NAME/KEY: cDNA encoding mutant urease αH219Q
    (B) LOCATION: Modification at position 1312 to glutamine
    (C) IDENTIFICATION METHOD: Sequencing
    (D) OTHER INFORMATION:

(xi) SEQUENCE DESCRIPTION: SEQ ID NO:1:

| | | | | | |
|---|---|---|---|---|---|
| CCCCGAATCT | GGCTGACTTA | AGAGAACGTT | ATGGAACTGA | CCCCCCGAGA | 50 |
| AAAAGACAAG | CTGTTGCTGT | TTACCGCCGC | GCTGGTGGCG | GAGCGTCGCC | 100 |
| TGGCCCGCGG | CCTGAAGCTC | AACTATCCGG | AGTCCGTGGC | CCTGATCAGC | 150 |
| GCCTTTATTA | TGGAAGGCGC | TCGGGACGGC | AAAAGCGTGG | CCTCGCTGAT | 200 |
| GGAGGAAGGC | CGTCACGTCC | TGACCCGCGA | GCAGGTGATG | GAGGGCGTCC | 250 |
| CGGAAATGAT | CCCGGATATC | CAGGTCGAAG | CCACCTTCCC | GGACGGCTCG | 300 |
| AAGCTGGTCA | CCGTTCACAA | CCCGATTATC | TGAGGTAGCG | CCATGATCCC | 350 |
| CGGTGAATAT | CACGTTAAGC | CCGGTCAGAT | AGCCCTGAAT | ACCGGCCGGG | 400 |
| CAACCTGTCG | CGTGGTCGTT | GAGAACCACG | GCGATCGGCC | GATTCAGGTC | 450 |
| GGTTCGCACT | ACCATTTCGC | CGAGGTTAAC | CCGGCGCTGA | AGTTCGACCG | 500 |
| TCAGCAGGCC | GCCGGCTATC | GCCTGAATAT | CCCGGCGGGC | ACGGCGGTAC | 550 |
| GCTTTGAACC | CGGCCAGAAA | CGCGAGGTCG | AGCTGGTGGC | CTTCGCCGGT | 600 |
| CACCGCGCCG | TCTTCGGCTT | CCGCGGCGAG | GTCATGGGCC | CTCTGGAGGT | 650 |
| AAACGATGAG | TAATATTTCA | CGCCAGGCCT | ATGCCGATAT | GTTCGGCCCC | 700 |
| ACCGTCGGCG | ACAAGGTGCG | CCTGGCAGAT | ACCGAGCTGT | GGATCGAGGT | 750 |
| GGAGGACGAT | TTGACCACCT | ACGGGGAAGA | GGTCAAATTC | GGCGGCGGCA | 800 |
| AAGTGATCCG | CGACGGCATG | GGCCAGGGAC | AGATGCTGGC | CGCCGACTGT | 850 |
| GTCGACCTGG | TGCTCACCAA | CGCGTTGATC | GTCGATCACT | GGGGGATCGT | 900 |
| TAAGGCCGAT | ATCGGCGTGA | AGGACGGCCG | GATCTTCGCC | ATCGGCAAAG | 950 |
| CCGGCAACCC | CGACATCCAG | CCCAACGTCA | CCATCCCCAT | CGGCGCTGCG | 1000 |
| ACGGAAGTGA | TCGCCGCCGA | AGGAAAAATT | GTCACCGCCG | GCGGGATCGA | 1050 |
| TACCCATATT | CACTGGATCT | GTCCGCAGCA | GGCGGAAGAG | GCGCTGGTCT | 1100 |
| CTGGCGTGAC | CACCATGGTC | GGCGGCGGCA | CCGGCCCGGC | CGCGGGCACC | 1150 |
| CATGCCACCA | CCTGCACCCC | GGGCCCGTGG | TATATCTCAC | GCATGCTGCA | 1200 |
| GGCGGCCGAC | AGCCTGCCGG | TCAATATCGG | CCTGCTGGGC | AAGGGAAACG | 1250 |
| TTTCTCAGCC | GGATGCCCTG | CGCGAGCAGG | TGGCGGCAGG | CGTTATTGGC | 1300 |
| CTGAAGATCC | AAGAGGACTG | GGGCGCCACC | CCGGCGGCGA | TCGACTGTGC | 1350 |

-continued

| | | | | | |
|---|---|---|---|---|---|
| GTTAACCGTC | GCCGATGAAA | TGGACATCCA | GGTCGCCCTG | CACAGCGACA | 1400 |
| CCCTGAATGA | ATCCGGTTTT | GTGGAAGACA | CCCTCGCCGC | CATCGGCGGG | 1450 |
| CGCACCATCC | ACACCTTCCA | TACCGAAGGG | GCCGGCGGCG | GCCATGCGCC | 1500 |
| GGACATCATC | ACCGCCTGCG | CCCACCCGAA | CATTTTGCCG | TCGTCCACCA | 1550 |
| ACCCAACGCT | GCCCTACACC | CTCAACACCA | TCGATGAACA | TCTCGATATG | 1600 |
| CTGATGGTCT | GCCACCATCT | GGACCCGGAC | ATCGCCGAGG | ACGTGGCCTT | 1650 |
| TGCCGAGTCG | CGCATTCGCC | GGGAAACCAT | CGCTGCGGAA | GACGTGCTGC | 1700 |
| ACGATCTCGG | CGCCTTCTCG | CTCACCTCCT | CCGATTCGCA | GGCCATGGGC | 1750 |
| CGCGTCGGGG | AAGTGATTCT | CCGCACCTGG | CAGGTGGCGC | ATCGCATGAA | 1800 |
| GGTGCAGCGC | GGAGCGCTGG | CGGAGGAGAC | CGGGGATAAC | GACAACTTCC | 1850 |
| GCGTGAAGCG | CTACATCGCC | AAATACACCA | TCAACCCGGC | GCTGACCCAC | 1900 |
| GGCATCGCAC | ACGAAGTCGG | ATCCATTGAG | GTGGGTAAGC | TGGCTGACCT | 1950 |
| CGTGGTCTGG | TCACCAGCCT | TCTTCGGCGT | GAAACCGGCC | ACCGTGATCA | 2000 |
| AAGGCGGCAT | GATCGCCATC | GCGCCGATGG | GCGATATCAA | TGCCTCTATT | 2050 |
| CCGACCCCGC | AGCCGGTGCA | CTACCGCCCG | ATGTTTGGCG | CGCTGGGCAG | 2100 |
| CGCCCGCCAT | CACTGCCGCC | TCACCTTCCT | GTCGCAGGCG | GCGGCAGCCA | 2150 |
| ATGGCGTTGC | CGAGCGGCTG | AACCTGCGCA | GCGCGATCGC | CGTGGTGAAA | 2200 |
| GGCTGCCGTA | CGGTGCAGAA | AGCCGACATG | GTGCACAACA | GTCTGCAGCC | 2250 |
| TAACATCACC | GTCGACGCCC | AGACCTATGA | GGTGCGGGTG | GATGGCGAAC | 2300 |
| TTATCACCAG | CGAGCCGGCA | GACGTTCTGC | CGATGGCGCA | ACGATATTTT | 2350 |
| CTGTTTTAAG | GAGAGCGGAT | GCTTTATTTA | ACTCAACGTC | TGGAGATCCC | 2400 |

( 2 ) INFORMATION FOR SEQ ID NO:2:

( i ) SEQUENCE CHARACTERISTICS:
        ( A ) LENGTH: 19
        ( B ) TYPE: nucleotides
        ( C ) STRANDEDNESS: Single
        ( D ) TOPOLOGY: Linear ( i i ) MOLECULE TYPE:
        ( A ) DESCRIPTION: oligonucleotide ( i i i ) HYPOTHETICAL: No ( i v ) ANTI-SENSE: No ( v i ) ORIGINAL SOURCE:
        ( A ) ORGANISM: N/A
        ( B ) STRAIN: N/A
        ( C ) INDIVIDUAL ISOLATE: N/A
        ( G ) CELL TYPE: N/A ( i x ) FEATURE:
        ( A ) NAME/KEY: glutaminyl mutating
        ( B ) LOCATION: nucleotide
        ( C ) IDENTIFICATION METHOD: Sequencing
        ( D ) OTHER INFORMATION: Synthetic
            oligonucleotide ( x i ) SEQUENCE DESCRIPTION: SEQ ID NO:2:

| | | |
|---|---|---|
| GAAGATCCAA | GAGGACTGG | 19 |

( 2 ) INFORMATION FOR SEQ ID NO:3:

( i ) SEQUENCE CHARACTERISTICS:
        ( A ) LENGTH: 100

(B) TYPE: amino acids
(C) STRANDEDNESS: Single
(D) TOPOLOGY: Linear (ii) MOLECULE TYPE:
(A) DESCRIPTION: Protein (iii) HYPOTHETICAL: No (iv) ANTI-SENSE: No (vi) ORIGINAL SOURCE:
(A) ORGANISM: N/A
(B) STRAIN: N/A
(C) INDIVIDUAL ISOLATE: N/A
(G) CELL TYPE: N/A (ix) FEATURE:
(A) NAME/KEY: subunit UreA
(B) LOCATION:
(C) IDENTIFICATION METHOD: Sequencing
(D) OTHER INFORMATION: encoded subunit of mutant urease (xi) SEQUENCE DESCRIPTION: SEQ ID NO:3:

```
                                Met  Glu  Leu  Thr  Pro
                                                    5

Arg  Glu  Lys  Asp  Lys  Leu  Leu  Leu  Phe  Thr  Ala
                    10                        15

Ala  Leu  Val  Ala  Glu  Arg  Arg  Leu  Ala  Arg  Gly
                    20                   25

Leu  Lys  Leu  Asn  Tyr  Pro  Glu  Ser  Val  Ala  Leu
          30                        35

Ile  Ser  Ala  Phe  Ile  Met  Glu  Gly  Ala  Arg  Asp
     40                        45

Gly  Lys  Ser  Val  Ala  Ser  Leu  Met  Glu  Glu  Gly
50                       55                        60

Arg  His  Val  Leu  Thr  Arg  Glu  Gln  Val  Met  Glu
                    65                        70

Gly  Val  Pro  Glu  Met  Ile  Pro  Asp  Ile  Gln  Val
               75                   80

Glu  Ala  Thr  Phe  Pro  Asp  Gly  Ser  Lys  Leu  Val
               85                   90

Thr  Val  His  Asn  Pro  Ile  Ile
     95                        100
```

(2) INFORMATION FOR SEQ ID NO:4:

(i) SEQUENCE CHARACTERISTICS:
(A) LENGTH: 106
(B) TYPE: amino acids
(C) STRANDEDNESS: Single
(D) TOPOLOGY: Linear (ii) MOLECULE TYPE:
(A) DESCRIPTION: protein (iii) HYPOTHETICAL: No (iv) ANTI-SENSE: No (vi) ORIGINAL SOURCE:
(A) ORGANISM: N/A
(B) STRAIN: N/A
(C) INDIVIDUAL ISOLATE: N/A
(G) CELL TYPE: N/A (ix) FEATURE:
(A) NAME/KEY: subunit UreB (B) LOCATION:
(C) IDENTIFICATION METHOD: Sequencing
(D) OTHER INFORMATION: encoded subunit (xi) SEQUENCE DESCRIPTION: SEQ ID NO:4:

```
                                        Met  Ile  Pro  Gly  Glu  Tyr
                                                                  5

His  Val  Lys  Pro  Gly  Gln  Ile  Ala  Leu  Asn  Thr  Gly  Arg
               10                       15

Ala  Thr  Cys  Arg  Val  Val  Val  Glu  Asn  His  Gly  Asp  Arg
20                       25                       30

Pro  Ile  Gln  Val  Gly  Ser  His  Tyr  His  Phe  Ala  Glu  Val
               35                  40                            45

Asn  Pro  Ala  Leu  Lys  Phe  Asp  Arg  Gln  Gln  Ala  Ala  Gly
                    50                            55

Tyr  Arg  Leu  Asn  Ile  Pro  Ala  Gly  Thr  Ala  Val  Arg  Phe
     60                       65                       70

Glu  Pro  Gly  Gln  Lys  Arg  Glu  Val  Glu  Leu  Val  Ala  Phe
               75                       80

Ala  Gly  His  Arg  Ala  Val  Phe  Gly  Phe  Arg  Gly  Glu  Val
85                       90                            95

Met  Gly  Pro  Leu  Glu  Val  Asn  Asp  Glu
               100                 105
```

(2) INFORMATION FOR SEQ ID NO:5:

(i) SEQUENCE CHARACTERISTICS:
        (A) LENGTH: 567
        (B) TYPE: amino acids
        (C) STRANDEDNESS: Single
        (D) TOPOLOGY: Linear (ii) MOLECULE TYPE:
        (A) DESCRIPTION: protein (iii) HYPOTHETICAL: No (iv) ANTI-SENSE: No (vi) ORIGINAL SOURCE:
        (A) ORGANISM: N/A
        (B) STRAIN: N/A
        (C) INDIVIDUAL ISOLATE: N/A
        (G) CELL TYPE: N/A (ix) FEATURE:
        (A) NAME/KEY: subunit UreC
        (B) LOCATION:
        (C) IDENTIFICATION METHOD: Sequencing
        (D) OTHER INFORMATION: Encoded subunit of mutant
            urease (xi) SEQUENCE DESCRIPTION: SEQ ID NO:5:

```
                                        Met  Ser  Asn  Ile  Ser
                                                             5

Arg  Gln  Ala  Tyr  Ala  Asp  Met  Phe  Gly  Pro  Thr  Val  Gly
               10                       15

Asp  Lys  Val  Arg  Leu  Ala  Asp  Thr  Glu  Leu  Trp  Ile  Glu
     20                       25                       30

Val  Glu  Asp  Asp  Leu  Thr  Thr  Tyr  Gly  Glu  Glu  Val  Lys
               35                       40

Phe  Gly  Gly  Gly  Lys  Val  Ile  Arg  Asp  Gly  Met  Gly  Gln
45                       50                       55
```

-continued

```
Gly Gln Met Leu Ala Ala Asp Cys Val Asp Leu Val Leu
         60                  65                    70

Thr Asn Ala Leu Ile Val Asp His Trp Gly Ile Val Lys
             75                  80

Ala Asp Ile Gly Val Lys Asp Gly Arg Ile Phe Ala Ile
     85                  90                  95

Gly Lys Ala Gly Asn Pro Asp Ile Gln Pro Asn Val Thr
            100                 105

Ile Pro Ile Gly Ala Ala Thr Glu Val Ile Ala Ala Glu
110                 115                 120

Gly Lys Ile Val Thr Ala Gly Gly Ile Asp Thr His Ile
         125                 130                 135

His Trp Ile Cys Pro Gln Gln Ala Glu Glu Ala Leu Val
                140                 145

Ser Gly Val Thr Thr Met Val Gly Gly Thr Gly Pro
     150                 155                 160

Ala Ala Gly Thr His Ala Thr Thr Cys Thr Pro Gly Pro
             165                 170

Trp Tyr Ile Ser Arg Met Leu Gln Ala Ala Asp Ser Leu
175                 180                 185

Pro Val Asn Ile Gly Leu Leu Gly Lys Gly Asn Val Ser
         190                 195                 200

Gln Pro Asp Ala Leu Arg Glu Gln Val Ala Ala Gly Val
                205                 210

Ile Gly Leu Lys Ile Gln Glu Asp Trp Gly Ala Thr Pro
     215                 220                 225

Ala Ala Ile Asp Cys Ala Leu Thr Val Ala Asp Glu Met
             230                 235

Asp Ile Gln Val Ala Leu His Ser Asp Thr Leu Asn Glu
240                 245                 250

Ser Gly Phe Val Glu Asp Thr Leu Ala Ala Ile Gly Gly
         255                 260                 265

Arg Thr Ile His Thr Phe His Thr Glu Gly Ala Gly Gly
                270                 275

Gly His Ala Pro Asp Ile Ile Thr Ala Cys Ala His Pro
     280                 285                 290

Asn Ile Leu Pro Ser Ser Thr Asn Pro Thr Leu Pro Tyr
             295                 300

Thr Leu Asn Thr Ile Asp Glu His Leu Asp Met Leu Met
305                 310                 315

Val Cys His His Leu Asp Pro Asp Ile Ala Glu Asp Val
         320                 325                 330

Ala Phe Ala Glu Ser Arg Ile Arg Arg Glu Thr Ile Ala
                335                 340

Ala Glu Asp Val Leu His Asp Leu Gly Ala Phe Ser Leu
     345                 350                 355

Thr Ser Ser Asp Ser Gln Ala Met Gly Arg Val Gly Glu
             360                 365

Val Ile Leu Arg Thr Trp Gln Val Ala His Arg Met Lys
370                 375                 380

Val Gln Arg Gly Ala Leu Ala Glu Glu Thr Gly Asp Asn
         385                 390                 395

Asp Asn Phe Arg Val Lys Arg Tyr Ile Ala Lys Tyr Thr
                400                 405
```

-continued

| | | | | | | | | | | | | |
|---|---|---|---|---|---|---|---|---|---|---|---|---|
| Ile | Asn | Pro | Ala | Leu | Thr | His | Gly | Ile | Ala | His | Glu | Val |
| | 410 | | | | | 415 | | | | | 420 | |
| Gly | Ser | Ile | Glu | Val | Gly | Lys | Leu | Ala | Asp | Leu | Val | Val |
| | | | 425 | | | | | 430 | | | | |
| Trp | Ser | Pro | Ala | Phe | Phe | Gly | Val | Lys | Pro | Ala | Thr | Val |
| 435 | | | | | 440 | | | | | 445 | | |
| Ile | Lys | Gly | Gly | Met | Ile | Ala | Ile | Ala | Pro | Met | Gly | Asp |
| | | 450 | | | | | 455 | | | | | 460 |
| Ile | Asn | Ala | Ser | Ile | Pro | Thr | Pro | Gln | Pro | Val | His | Tyr |
| | | | | 465 | | | | | 470 | | | |
| Arg | Pro | Met | Phe | Gly | Ala | Leu | Gly | Ser | Ala | Arg | His | His |
| | 475 | | | | | 480 | | | | | 485 | |
| Cys | Arg | Leu | Thr | Phe | Leu | Ser | Gln | Ala | Ala | Ala | Ala | Asn |
| | | | 490 | | | | | 495 | | | | |
| Gly | Val | Ala | Glu | Arg | Leu | Asn | Leu | Arg | Ser | Ala | Ile | Ala |
| 500 | | | | | 505 | | | | | 510 | | |
| Val | Val | Lys | Gly | Cys | Arg | Thr | Val | Gln | Lys | Ala | Asp | Met |
| | | 515 | | | | | 520 | | | | | 525 |
| Val | His | Asn | Ser | Leu | Gln | Pro | Asn | Ile | Thr | Val | Asp | Ala |
| | | | | 530 | | | | | 535 | | | |
| Gln | Thr | Tyr | Glu | Val | Arg | Val | Asp | Gly | Glu | Leu | Ile | Thr |
| | 540 | | | | | 545 | | | | | 550 | |
| Ser | Glu | Pro | Ala | Asp | Val | Leu | Pro | Met | Ala | Gln | Arg | Tyr |
| | | | 555 | | | | | 560 | | | | |
| Phe | Leu | Phe | | | | | | | | | | |
| 565 | | | | | | | | | | | | |